US005616753A

United States Patent [19]
Turner et al.

[11] Patent Number: 5,616,753
[45] Date of Patent: Apr. 1, 1997

[54] STABILIZERS FOR UNSATURATED, POLYMERIZABLE ORGANOSILICON COMPOUNDS

[75] Inventors: Scot M. Turner; James S. Ritscher, both of Marietta, Ohio; Michael Hallden-Abberton, Maple Glen, Pa.; Donald McLeod, Jr., Briarcliff Manor, N.Y.

[73] Assignee: OSi Specialties, Inc., Danbury, Conn.

[21] Appl. No.: 406,604

[22] Filed: Mar. 20, 1995

[51] Int. Cl.$^6$ .................................................. C07F 7/08
[52] U.S. Cl. ................................................... 556/401
[58] Field of Search .................................... 532/401

[56] References Cited

U.S. PATENT DOCUMENTS

| | | | |
|---|---|---|---|
| 3,803,140 | 4/1974 | Cook et al. | 556/401 |
| 3,925,434 | 9/1975 | Chuang | 556/401 |
| 4,670,131 | 6/1987 | Ferrell . | |
| 4,780,555 | 10/1988 | Bank | 556/401 X |
| 4,798,889 | 4/1989 | Pleudemann et al. . | |
| 5,103,032 | 4/1992 | Turner et al. . | |
| 5,436,345 | 7/1995 | Lewis et al. . | |

FOREIGN PATENT DOCUMENTS 0178168  4/1986  European Pat. Off. .

OTHER PUBLICATIONS

Indrichan, K.M. et al., Formation of Stable Radicals Upon The Photolysis, etc., Institute of Chemistry, Acadamy of Sciences, etc., No. 7, pp. 1664–1667, (Jul. 1985).

Allayarov, S.R. et al., Formation of Stable Radicals Upon the Photolysis of Perfluoro, etc., Branch of the Institute of Chemical Physics, Acadamy of Sciences, etc., No. 10, pp. 2359–2361, (Oct. 1986).

Catalog Handbook of Fine Chemicals, Aldrich Chemical Co., pp. 1572–1579, 1992.

Spin Labels and Spin Traps, Sigma Chemical Co., (1995).

Quantitative Aspects of Synergistic Inhibition of Oxygen, etc., Journal of Polymer Science, (vol. 18), pp. 1139–1145 (1982).

Nicolson, A., "The Effect of $O_2$ Concentration on Methacrylic Acid Stability", (Vol. 10, No. 3), pp. 171–183, (1991).

Evans, C.A., Spin Trapping, Aldrichinica Acta, (vol. 12, No. 2), (1979).

*Primary Examiner*—Paul F. Shaver

[57] ABSTRACT

The present invention describes a method for inhibiting the polymerization of unsaturated silanes by the addition of a non-aromatic stable free radical during any of the steps of the formation of the desired silane, the purification of the desired silane, and to the desired silanes, as well as compositions of the inhibitors and the silanes. Particular classes of silanes to be inhibited include acryloxy-, methacryloxy-, and vinyl- functional silanes. The free radicals for use as inhibitors include various nitroxides. The free radicals taught herein are effective as inhibitors at elevated temperatures, for extended periods of time, and even in the absence of molecular oxygen.

19 Claims, No Drawings

STABILIZERS FOR UNSATURATED, POLYMERIZABLE ORGANOSILICON COMPOUNDS

BACKGROUND OF THE INVENTION

Olefinically modified silanes, e.g., vinyltriethoxysilane, 3-(meth)acryloxypropyltrimethoxysilane and the like, are useful as coupling agents in applications where molecular bonding of inorganic substrates and fillers with organic resins and polymers is required. However, these silanes have a tendency to homopolymerize during production, purification and in situ prior to application. Thus, inhibitors are required to prevent such polymerization.

The prior art has taught the use of phenols, such as MEHQ (p-methoxyphenol), and aromatic amines as inhibitors for these polymerizable silanes. See for example U.S. Pat. No. 5,103,032 to Turner et al. However, such inhibitors are disadvantageous in that, at their required levels of use, they absorb ultra-violet light, turn yellow, and undergo photooxidation. In addition, many traditional polymerization inhibitors have relatively high boiling points, restricting their utility as co-boiling inhibitor candidates. Also, many traditional inhibitors, being non-polar, can cause failure of the final silane to pass stringent water solubility requirements— especially at the typical required inhibitor concentrations.

Another problem with phenolic inhibitors is that they require oxygen to work effectively (an amount commensurate with the amount of inhibitor), yet, not too much oxygen because excessive oxygen will form peroxides and thus initiate polymerization reactions. Therefore, phenolic inhibitors require that the level of oxygen be carefully controlled.

Relatedly, the literature also describes the use of piperidinyloxy free radicals as antioxidants for the stabilization of (meth)acrylic acids and esters, as well as other reactive olefin compounds at relatively high levels, 100 to 500 ppm, often in conjunction with a quinone or phenolic co-inhibitor. See for example U.S. Pat. No. 5,254,760 to Winter et al. However, the prior art does not disclose the use of such inhibitors with silanes nor at low levels which would provide the advantages of the present invention.

SUMMARY OF THE INVENTION

This invention describes the use of non-aromatic stable free radicals as polymerization inhibitors for unsaturated, polymerizable silanes and the compositions so formed. The present invention also describes a method for inhibiting the polymerization of the silanes by the addition of these free radicals during any of the stages of the formation of the desired silane, to the crude reaction product during purification and to the final product for shelf life enhancement. Particular classes of silanes to be inhibited include acryloxy-, methacryloxy-, and vinyl-functional silanes. Particular free radicals for use as stabilizers include nitroxides. The nitroxides taught herein are effective as inhibitors at elevated temperatures, for extended periods of time, and even in the absence of molecular oxygen.

DETAILED DESCRIPTION OF THE INVENTION

The unsaturated, polymerizable silanes contemplated to be inhibited from polymerization herein are those which have an unsaturated group, e.g., a vinyl, acryl, or methacryl, thereon which are capable of polymerization. The silanes include alkoxysilanes, alkylsilanes, bis-silanes, halogenated silanes and other silanes as are used in the art for coupling agents. Particular classes of silanes contemplated herein are: vinyl silanes, methacryloxy silanes, and acryloxy silanes.

The methacryloxy- and acryloxy- silanes may be represented by the formula $[CH_2=CRC(O)O(R'O)_a(R'')_b]_c\text{-}SiY_{4-c}$ where R is a hydrogen or methyl, R' is a branched or linear alkylene of 2 to 4 carbon atoms, R" is branched or linear alkylene of 1 to 11 carbon atoms; Y is a methyl, halide, alkoxy or alkoxy substituted alkoxy group where the alkoxy has 1 to 4 carbon atoms: a is 0 to 10; b=0 or 1; a+b=1 to 11; and c=1 or 2. The vinyl silanes may be represented by the structure $[CH_2=CH]_cSiY_{4-c}$ or $[CH_2=CHR''']_cSiY_{4-c}$, where R''' is a branched or linear alkylene group of 1 to 8 carbon atoms or an aryl group (which itself may be attached through an alkyl group); and Y and c are defined as above.

Particular silanes for use herein are: vinyltriethoxy silane, vinylmethyldimethoxy silane, vinylmethyldiethoxy silane, vinyldimethylmethoxy silane, vinyltriisobutoxysilane, 3-methacryloxypropyl-trimethoxy silane, 3-acryloxypropyltrimethoxy silane, 3-methacryloxypropyltriethoxy silane, 3-methacryloxypropyl[tris(beta-methoxyethoxy)]silane, 3-methacryloxypropyldimethoxymethyl silane, 3-methacryloxypropylmethoxydimethyl silane, 2-acryloxyethyltriisopropoxy silane, 3-methacryloxyethyltriisobutoxy silane, 3-methacryloxytrioctyloxy silane, 3-methacryloxypropyldiethoxymethyl silane and 3-methacryloxytrioctyloxy silane, 3-methacryloxypropyldiethoxymethyl silane and 3-methacryloxy-propyltrichloro silane. These silanes may be prepared as is well known in the art. See for example U.S. Pat. Nos. 3,258,477 to Plueddemann et al. and 4,709,067 to Chu and *Comprehensive Handbook on Hydrosilylation*, Marciniec, ed. (1992).

The non-aromatic stable free radicals contemplated for use herein are nitroxides, i.e, compounds with at least one N-O● functionality thereon. Examples of nitroxide radicals are dialkyl nitroxides ($[R^1R^2NO●]$ where $R^1$ and $R^2$ are alkyl groups of $C_2$ to $C_8$ which are branched or linear and which may have substituents thereon), proxyls [N-oxide cycloazopentane or pyrrolidine N-oxide], doxyls [N-oxide cycloazo-3-oxapentane or oxazolidine N-oxyl], and piperidinyloxy free radicals [N-oxide cycloazohexane or piperidine N-oxyl]. The most useful nitroxides, particularly TEMPO and derivatives, generally have tertiary carbon groups attached to the nitrogen atoms of the nitroxide groups.

Specific examples of nitroxides include di-tert-butyl nitroxide, tert-amyl tert-butyl nitroxide, 2,2,5,5-tetramethylpyrrolidine-N-oxyl, and 4,4-dimethyl-3-oxazolidine N-oxyl. The most preferable nitroxides are the piperidinyloxy free radicals, particularly, TEMPO (2,2,6,6-tetramethylpiperidine-N-oxyl), 4-hydroxy-TEMPO (4-hydroxy-2,2,6,6-tetramethylpiperidine-N-oxyl), and 4-hydroxy TEMPO benzoate, all commercially available from Aldrich Chemicals of Milwaukee, Wis. The other nitroxides may be manufactured as is well known in the art. See for example Keany, J., *Chem. Rev.*, 78, 37 (1978).

The nitroxides may convert to hydroxyl amines under certain process conditions and these amines do exhibit inhibitor effectiveness, though not as good as the nitroxides. However, such hydroxyl amines are contemplated as being within the present invention.

Moreover, nitroxide free radicals may be created in situ and such compositions are contemplated herein as well. Specifically such conversions occur from amine oxides and nitroso compounds. For example, nitroso t-butane (t-butyl-N=O) readily converts to a di-t-butyl nitroxide, and 5,5 dimethyl-1-pyrroline-N-oxide to a 2,2 dimethyl-5-substituted nitroxide radical, by reaction with a free radical.

The stabilization is effected by employing the free radicals in an amount at least sufficient to prohibit polymerization of the silane. The particular amount used depends largely on the severity of the conditions to which the silane is subjected during its initial formation, purification and storage. Further, the higher the temperature, or in the absence of dissolved oxygen, the greater the amount of free radical inhibitor required. Moreover, the amount of radical required during distillation, the preferred method of purification of silanes, depends largely on the distillation conditions, e.g., pressure, temperature, column height and reflux ratio, etc. Generally, the greater the system pressure, the higher the distillation temperature and therefore, the greater the required amount of free radical inhibitor.

Typically, concentrations of free radicals of 0.1–25 ppm, preferably 1–10 ppm, are sufficient to stabilize polymerizable silanes for long periods with or without dissolved oxygen and at elevated temperatures. Higher concentrations may be used but are undesirable because as concentration increases, the likelihood of the free radical interfering with downstream applications, including detrimental effects on product color, product solubility or reactivity of the product, increases. Exemplary is vinyltriethoxysilane which was stabilized at 100° C. for two hours with 0.2 ppm levels of TEMPO and 4-hydroxy-TEMPO, with and without dissolved oxygen. Lower concentrations may be used in silanes which are relatively stable toward polymerization.

The non-aromatic stable free radicals give a clear advantage as to time of stability over prior art inhibitors. Generally, at room temperature, the free radicals will keep the polymerizable silanes stable for many months. With agitation and heating (e.g., 140° C.), the inhibited composition can have a shelf life of greater than 220 hours.

Another advantage of the present invention is that the free radicals prevent polymerization even at elevated temperatures, i.e., up to 160° C. For example, it was observed that at 500 ppm 4-hydroxy-TEMPO and at 100 ppm 4-hydroxy-TEMPO, no gelation occurred with γ-methacryloxypropyl-trimethoxysilane at conditions of 140° C. without dissolved oxygen (or with oxygen in the headspace of the test systems)—even after 280 and 264 hours, respectively.

The stability of the inhibited compositions also occurs in the absence of oxygen. With or without dissolved oxygen, the inhibited product is stable for months at ambient temperature. The prior art inhibitors, however, required the presence of controlled low levels of oxygen to maintain effectiveness.

The inhibited compositions of the present invention may contain more than one polymerizable silane as well as other components, including other inhibitors known in the art, catalysts and other polymerizable monomers. The free radicals generally are added to the silanes as liquids or solid powders or as dilute solutions in appropriate solvents.

Non-aromatic stable free radicals are of great utility not only as stabilizers of silanes for storage, but also as stabilizers in the production of the silanes, e.g., during hydrosilation, silyl-esterification and silyl-transesterification reactions. During the production of the unsaturated silanes of the present invention, there generally tend to be two types of polymerization problems, the polymerization of the product as it is formed and the polymerization of any unreacted starting material. The free radical prevents both such polymerizations during reaction.

Moreover, the stable free radicals may be present during the purification of the silane from the excess reactants and impurities, e.g., unreacted olefins. This separation generally has been accomplished by distillation. Nitroxides with various boiling points and molecular weights are available commercially and as a result, a nitroxide can be selected based on its boiling point to provide co-distillative inhibition during distillation processing. Thus, given that the nitroxides also stabilize the olefinic starting material, both a low boiling "lights" stream and a high boiling "heavies" stream can be suitably stabilized through the proper selection of the nitroxide. Accordingly, blends of nitroxides and/or nitroxide precursors may be employed for reasons including having nitroxides present with a range of boiling points.

Nitroxides which contain OH functionality have the distinct advantage of maintaining effective polymerization inhibition of alkoxy-functional silanes even if silyltransesterification occurs. Thus, a co-boiling nitroxide also has the capability to function as a liquid phase inhibitor by in-situ derivation of the alkoxy-functional silanes, which is particularly useful during distillation procedures. In this case, although some of the radical co-distills with product, some more of the radical can react with the product to become a high-boiling inhibitor, both of which stabilize the heavies stream. Normally, phenolic inhibitors have the drawback of being slowly consumed by the silane as silyl-transesterification gradually takes place during processing or storage because of the consumption of the phenolic C-OH group with formation of a C-O-Si siloxy group, which can render the moiety inactive as a polymerization inhibitor.

During production of polymerizable silanes, the stable free radicals may also be used as emergency or stop-gap inhibitors. Thus, if a reaction begins to get out of control or a sample begins to polymerize where such polymerization is undesirable, the free radical may be added to the already polymerizing sample to stop the polymerization.

Another distinct advantage of nitroxides (over traditional phenolic and aromatic amine polymerization inhibitors) is that they do not absorb ultra-violet light and do not photo-oxidize. Likewise, the free radicals contemplated herein do not impart noticeable color to the distilled product in the concentrations employed. For example, employing a Platinum-Cobalt color measurement, less than 5 Pt-Co color is imparted to the final product with typical concentrations of use of 4-hydroxy-TEMPO. Further, the free radicals do not interfere with water solubility characteristics of the silane product—especially at the concentrations employed. Thus, the inhibited silanes present clear solutions for use for applications where such clarity is required.

One exemplary use is in polymer coatings for colored paints. With prior art inhibitors, photo-degradation often occurred at the interface between the layer of the coating and the paint. Given the low dosage necessary and the clarity achieved therewith, said problems can be avoided with the use of the present invention.

An exemplary use for compositions of the present invention is in food packaging. By minimizing the amount of inhibitor necessary in clear food wrappings, there is a commensurate minimization in migration of unwanted chemicals into the food.

The inhibited silane compositions may also be used in RTV (room temperature vulcanizable) sealants. Unlike prior art inhibitors, the low amounts of the nitroxides do not undergo reactions with the chemicals in the RTV sealant and therefore, do not affect the color of said sealant. This is also true of using the inhibited silanes in countertop (e.g., in kitchens) formulations where color is of importance. The present invention is also useful as primers for such sealants, as well as for adhesives.

The following illustrative and comparative examples are intended to describe the present invention in more detail; however, they are not meant to limit the scope of the specification and the claims.

EXAMPLES

1. A 50 gram sample of freshly distilled, uninhibited 3-methacryloxypropyltrimethoxysilane was charged to a 2 oz. glass vessel together with 500 ppm 4-hydroxy-TEMPO, deoxygenated, sealed, and maintained at 140° C. with continuous agitation. Gelation did not occur after 280 hours. The temperature of 140° C. represents the probable maximum temperature to which the silane would be exposed during preparation, purification, or use.
2. Example #1 was repeated but utilizing 100 ppm of 4-hydroxy-TEMPO. Gelation did not occur after 264 hours.
3. Example #1 was repeated but utilizing 50 ppm 4-hydroxy-TEMPO. Gelation did not occur after 117 hours.
4. Example #1 was repeated but utilizing 25 ppm 4-hydroxy-TEMPO. Gelation did not occur after 189 hours.
5. Example #1 was repeated but utilizing 10 ppm 4-hydroxy-TEMPO. Gelation occurred in 227 hours.
6. Example #1 was repeated but utilizing 5.1 ppm 4-hydroxy-TEMPO. Gelation occurred in 125 hours.
7. Example #6 was repeated but without the deoxygenation step. The liquid phase was sparged with 3% $O_2/N_2$ prior to sealing the vessel. Gelation occurred in 88 hours.
8. (Comparative) Example #1 was repeated but without the addition of 4-hydroxy-TEMPO. Gelation occurred in 2.8 hours.
9. Example #1 was repeated except 5.1 ppm TEMPO was used instead of 4-hydroxy-TEMPO. Gelation occurred in 153 hours.
10. Example #6 was repeated except 5.1 ppm 4-amino-TEMPO was used instead of 4-hydroxy-TEMPO. Gelation occurred in 147 hours.
b 11. Example #10 was repeated but utilizing 1.6 ppm 4-amino-TEMPO. Gelation occurred in 26 hours.
12. Example #6 was repeated except 2.1 ppm 4-hydroxy-TEMPO was used. Gelation occurred in 45 hours.
13. Example #12 was repeated except 2.1 ppm TEMPO was used instead of 4-hydroxy-TEMPO. Gelation occurred in 39 hours.
14. Example #11 was repeated except 2.0 ppm 4-amino-TEMPO was used. Gelation occurred in 41 hours.
15. (Comparative) Example #1 was duplicated except that 1000 ppm of p-methoxyphenol was used as the only inhibitor. Gelation occurred in 10 hours.
16. (Comparative) Example #1 was duplicated except that 1000 ppm of 2,6-di-t-butyl-4-methylphenol was used as the only inhibitor. Gelation occurred in 28 hours.
17. Three 10.0 gram samples of vinyltriethoxysilane were prepared using 0, 0.1, and 0.2 ppm of 4-hydroxy-TEMPO, and then each were heated for 2 hours at 100° C. A solution was made from a 10:43:5 ratio of each vinyltriethoxysilane, methanol, and water. A "haze" measurement utilizing a Hach turbidimeter revealed "Hach numbers" of 44, 12.1, and 0.42, respectively. This compares to an ideal control sample of vinyltriethoxysilane which registers 0 Hach, translating to no haze.
18. (Comparative) Three 20 gram samples of vinyltriethoxysilane were prepared using 0, 5, and 10 ppm 2,6-di-t-butyl-4-methylphenol (BHT), then heated for 2 hours at 100° C. The haze measurement (described in example #17) revealed Hach numbers of 45, 34, and 0.37, respectively. Thus, worse results were obtained, while using more inhibitor.
19. Example #1 was repeated, but utilizing 6.9 ppm di-t-butyl nitroxide. Gelatin occurred in 29 hours.
20. Example #1 was repeated, but utilizing 5.0 ppm 3-cyanoproxyl free radical. Gelatin occurred in 83 hours.
21. Example #1 was repeated, but utilizing 5.0 ppm t-amyl t-butyl nitroxyl free radical. Gelatin occurred in 24 hours.
22. Example #1 was repeated, but utilizing 5.2 ppm 4-oxo-TEMPO. Gelatin occurred in 108 hours.
23. Example #1 was repeated, but utilizing 5.0 ppm 4-cyano-TEMPO. Gelatin occurred in 58 hours.
24. Example #1 was repeated, but utilizing 41.7 ppm N,N-diethylhydroxylamine. Gelatin occurred after 39.2 hours.
25. A 50 liter glass batch distillation system fitted with packed column, water condenser, refrigerated condenser and vacuum source was charged with 140 lbs. of crude 3-methacryloxypropyltrimethoxysilane (about 90% pure) which was prepared using only high boiling aromatic inhibitors. To this crude material was added 9 ppm of 4-hydroxy TEMPO. The low boiling components were stripped off and the crude was inhibited with an additional 5 ppm 4-hydroxy-TEMPO and 5 ppm TEMPO. The crude was then distilled at about 100° C./3 mm Hg with 110°–130° C. pot temperature to yield 117 lbs. of 99% pure 3-methacryloxypropyl-trimethoxysilane. Product aliquots were deoxygenated and subjected to 140° C. with continuous stirring (as described in Example #1). Gelation occurred in 133 hours.

We claim:

1. An inhibited silane composition comprising a polymerizable silane and a non-aromatic stable free radical in an amount sufficient to inhibit the silane.

2. A composition according to claim 1 wherein the free radical is present at 0.05 to 50 ppm.

3. A composition according to claim 1 wherein the free radical is a nitroxide.

4. A composition according to claim 3 wherein the nitroxide is derived in situ from a nitroso compound.

5. A composition according to claim 3 wherein the nitroxide is derived in situ from an amine oxide.

6. A composition according to claim 3 wherein the free radical is selected from the group of: dialkyl nitroxides, proxyls, doxyls, and piperidinyloxy free radicals.

7. A composition according to claim 6 wherein the free radical is selected from the group consisting of 2,2,6,6 tetramethylpiperidinyloxy free radical, 4-hydroxy-2,2,6,6-tetramethylpiperidinyloxy free radical, di-tert-butyl nitroxide, tert-amyl tert-butyl nitroxide, 2,2,5,5-tetramethylpyrrolidine-N-oxyl, and 4,4-dimethyl-3-oxazolidine N-oxyl.

8. A composition according to claim 1 wherein the polymerizable silane is selected from the group of: vinyl silanes, acryloxy silanes and methacryloxy silanes.

9. A composition according to claim 8 wherein the silane is selected from the group consisting of: vinyltriethoxy silane, vinylmethyldimethoxy silane, vinylmethyldiethoxy silane, vinyldimethylmethoxy silane, vinyltriisobutoxysilane, 3-methacryloxypropyl-trimethoxy silane, 3-acryloxypropyltrimethoxy silane, 3-methacryloxypropyltriethoxy silane, 3-methacryloxypropyl[tris(beta-methoxyethoxy)] silane, 3-methacryloxypropyl-dimethoxymethyl silane, 3-methacryloxypropylmethoxydimethyl silane, 2-acryloxyethyltriisopropoxy silane, 3-methacryloxyethyltriisobutoxy silane, 3-methacryloxytrioctyloxy silane, 3-methacryloxypropyldiethoxymethyl silane and 3-methacryloxypropyl-trichloro silane.

10. A composition according to claim 9 wherein the composition is stable to polymerization for at least 2 days at 140° C.

11. A composition according to claim 10 wherein the composition is stable to polymerization for at least three months at room temperature.

12. A composition according to claim 1 wherein the composition is stable to polymerization for at least 3 months in the absence of molecular oxygen.

13. A method for inhibiting the polymerization of a polymerizable silane comprising adding to a polymerizable silane an inhibitor comprising a non-aromatic stable free radical.

14. A method according to claim 13 wherein the non-aromatic stable free radical is a nitroxide.

15. A method according to claim 14 wherein the non-aromatic stable free radical is selected from the group of: dialkyl nitroxides, proxyls, doxyls, and piperidinyloxy free radicals.

16. A method according to claim 15 wherein the free radical is selected from the group consisting of 2,2,6,6 tetramethylpiperidinyloxy free radical, 4-hydroxy-2,2,6,6-tetramethylpiperidinyloxy free radical, di-tert-butyl nitroxide, tert-amyl tert-butyl nitroxide, 2,2,5,5-tetramethylpyrrolidine-N-oxyl, and 4,4-dimethyl-3-oxazolidine N-oxyl.

17. A method according to claim 13 wherein the polymerizable silane is selected from the group of: vinyl silanes, acryloxy silanes and methacryloxy silanes.

18. A method according to claim 17 wherein the silane is selected from the group of: vinyltriethoxy silane, vinylmethyldimethoxy silane, vinylmethyldiethoxy silane, vinyldimethylmethoxy silane, vinyltriisobutoxysilane, 3-methacryloxypropyl-trimethoxy silane, 3-acryloxypropyltrimethoxy silane, 3-methacryloxypropyltriethoxy silane, 3-methacryloxypropyl[tris(beta-methoxyethoxy)]silane, 3-methacryloxypropyldimethoxymethyl silane, 3-methacryloxypropylmethoxydimethyl silane, 2-acryloxyethyltriisopropoxy silane, 3-methacryloxyethyltriisobutoxy silane, 3-methacryloxytrioctyloxy silane, 3-methacryloxypropyldiethoxymethyl silane and 3-methacryloxy-propyltrichloro silane.

19. A method according to claim 13 wherein the adding of the inhibitor is done during a polymerizable silane processing step selected from the group consisting of: silane formation, purification and storage.

* * * * *